United States Patent [19]

Fusey

[11] 3,943,066

[45] Mar. 9, 1976

[54] PREPARATION OF COMPOSITION FOR MAKING HYDROCARBON AND FATS INTO BIODEGRADABLE EMULSIONS

[75] Inventor: Pierre Fusey, Paris, France

[73] Assignee: Banque Pour L'Expansion Industrielle "Banexi", Paris, France

[22] Filed: May 10, 1974

[21] Appl. No.: 468,883

[30] Foreign Application Priority Data

May 22, 1973 France ............................ 73.18559

[52] U.S. Cl. ................ 252/356; 252/357; 252/545; 252/546; 252/111; 252/118; 252/DIG. 6
[51] Int. Cl.$^2$. C11D 9/02; C11D 9/34; B01F 17/16; B01F 17/00
[58] Field of Search.... 252/356, 117, 118, 545–546, 252/DIG. 6, DIG. 14, DIG. 17, 357, 111; 210/DIG. 21

[56] References Cited
UNITED STATES PATENTS

| | | | |
|---|---|---|---|
| 1,598,664 | 9/1926 | Teach ................................. | 252/118 |
| 2,094,609 | 6/1936 | Kritchevsky .................... | 252/357 X |
| 2,208,524 | 1/1936 | Darsey et al. .................... | 252/118 X |
| 2,274,807 | 3/1942 | Rawlins et al. ................. | 252/357 X |
| 2,586,496 | 2/1952 | Young et al. ...................... | 252/117 |
| 2,679,504 | 5/1954 | Katzman ........................... | 252/357 X |
| 3,175,949 | 3/1965 | Siegal................................. | 252/357 X |
| 3,244,638 | 4/1966 | Foley et al. ...................... | 252/357 X |

OTHER PUBLICATIONS

McCutcheon: *Detergents and Emulsifiers*, John W. McCutcheon, Inc.; 1967, pp. 102 and 181.
Morrison and Boyd: *Organic Chemistry;* Allyn and Bacon, 1966; p. 590.
*The Condensed Chemical Dictionary;* Litton Educational Publishing, Inc.; 1971; p. 380.

*Primary Examiner*—Benjamin R. Padgett
*Assistant Examiner*—David Leland
*Attorney, Agent, or Firm*—Young & Thompson

[57] ABSTRACT

The present invention concerns the preparation of a composition for making hydrocarbons and fats into biodegradable emulsions and the preparation thereof. This composition is formed substantially by aliphatic amide or carboxylic acid ester of an aliphatic amide, an ammonium salt of a carboxylic acid, a phosphoaminolipid and a petroleum solvent free from benzenic fractions. This process comprises reacting an excess of a a carboxylic acid with a primary or secondary aliphatic amine or amino-alcohol, neutralising the mixture by the addition of ammonia to bring the pH to 7, and finally adding to the neutralised mixture a phospho-aminolipide and a benzenic fraction-free petroleum solvent.

6 Claims, No Drawings

PREPARATION OF COMPOSITION FOR MAKING HYDROCARBON AND FATS INTO BIODEGRADABLE EMULSIONS

The elimination of hydrocarbon wastes and mineral, animal or vegetable fats by biological degradation gives rise to problems since natural biodegradation is very slow. It is known that in order to accelerate the biodegradation of hydrocarbons or facts by micro-organisms, one must supply the microorganisms with sources of nitrogen and phosphorus which, in addition to the carbon supplied by the products to be removed, permit the development and growth of micro-organisms. In the case of biodegradation in a closed environment i.e. in a fermenter or in a vat, it is sufficient to use an aqueous culture medium containing the various nutrient elements either in solution or in suspension. On the other hand, research has shown that in the case of very dilute media such as, for example, spillages or wastes on the sea or on a river, the nitrogen- and/or phosphorus-supplying substances must be bonded with the hydrocarbon molecules and form an emulsion therewith. If this is not the case the substances are so diluted as to be practically equivalent to their natural content in the water so that the rate of degradation approximates to that of natural biodegradation.

It is, therefore, necessary that a product used to promote hydrocarbon biodegradation be capable of forming an aqueous emulsion which emulsion contains not only the product to be biodegraded but also molecules of the substances for supplying nitrogen and phosphorus.

Further, the composition formed by the nitrogen- and/or phosphorus containing substances must have a detergent power in order to clean surfaces soiled by the products to be eliminated or degraded. Finally, the composition should not, itself, be toxic towards the fauna or flora.

The composition for forming hydrocarbons and fats into a biodegradable aqueous emulsion comprises an aliphatic amide or a carboxylic ester of an aliphatic amide, an ammonium salt of a carboxylic acid, a phospho-aminolipide and a petroleum solvent free from benzenic fractions. Preferably, the composition contains from 20 to 34% by weight of aliphatic amide or aliphatic amide carboxylic acid ester, from 2.5 to 6% by weight of carboxylic acid ammonium salt, from 2.5 to 5% by weight of phospho-aminolipide and from 55% to 75% by weight of benzene fraction-free petroleum solvent. The composition in accordance with the invention may be prepared by reacting an excess of a carboxylic acid with a primary or secondary aliphatic amine or a primary or secondary aliphatic amino-alcohol neutralising the mixture by the addition of ammonia to bring the pH to about 7, and adding thereto the phospho-aminolipide and then the benzene fraction-free petroleum solvent. The amine may be, for example mono-ethylamine, diethylamine, monomethylamine, dimethylamine, dodecylamine, isopropylamine, n-butylamine, di-n-butylamine, monoamylamine, di-n-amylamine or di-iso-amylamine.

Suitable aliphatic amino-alcohols include, for example, mono-ethanolamine, diethanolamine, amino-propanol and amino-butanol.

The aliphatic carboxylic acid is preferably a fatty acid which is liquid at ambient temperature such as, for example, acetic acid, propionic acid, n-butyric acid, hexanoic acid, caprylic acid, 2-ethyl-hexanoic acid, oleic acid, capric acid or linoleic acid or a hydroxy acid such as lactic acid or ricinoleic acid.

The phospho-aminolipid acid will generally be lecithin.

The petroleum solvent may be white spirit free from benzene fractions, n-hexane, n-heptane, n-octane, petroleum ether, a heavy non-benzenic solvent or a mixture of such products.

In the compositions of the invention, the amide, and particularly the aliphatic amide carboxylic acid ester serves as detergent, its detergent power probably being greater than that of the corresponding amines due to the presence of a carbonyl group and, further, the amide also supplies a part of the necessary nitrogen. Because of its two lypophilic and hydrophilic radicals the amide ensures the stability of the emulsion. The ammonium salt forms a source of nitrogen and the lecithin provides the necessary phosphorus.

The following examples illustrate the preparation of the compositions in accordance with the invention and their application. In the examples the parts are parts by weight unless otherwise stated.

EXAMPLE 1

7.5 parts of mono-ethanolamine and 36 parts by weight of 2-ethylhexanoic acid are mixed with stirring and then neutralised with ammonia to bring the pH of the mixture to 7.

5 parts of lecithin and 102 parts of white spirit are added to 46 parts of the mixture (corresponding to 40 parts of 2-ethyl hexanoic ethanolamide 2-ethylhexanoate and 6 parts by weight of ammonium 2-ethyl-hexanoate).

The composition was used to treat a sheet of hydrocarbon floating on an aquarium comprising a body of soft water, the composition being used in an amount of from 15 to 20 parts per 100 parts of hydrocarbon. An emulsion formed which floated in the upper layers of the aquarium. The flora and fauna of the aquarium showed no ill effects due to the presence of the emulsion which progressively disappeared. Gas phase chromatography showed complete biodegradation within six weeks.

EXAMPLE 2

7.5 parts of monoethanolamine and 18 parts of 2-ethyl-hexanoic acid were mixed with stirring after which there were added thereto 35 parts of oleic acid and the whole neutralised to pH 7 by the addition of ammonia. There were thus obtained ethanolamide 2-ethyl-hexanoic oleate and ammonium oleate.

18% of lecithin and 250% of ligroin (or petroleum ether) free of benzene fractions were added to this mixture.

The composition obtained was used to clean a floor soiled with No. 2 fuel which had accumulated and oxidised over a long time. The rinsing waters containing the emulsion were recovered and their non-toxicity towards flora and fauna and their biodegradability were verified. All trace of hydrocarbon was removed from the floor.

EXAMPLE 3

9 parts of diethylamine were mixed with 21.5 parts of capric acid and the whole neutralised with ammonia.

The mixture of capric diethylamide and ammonium caproate was mixed with lecithin and white spirit to obtain a composition containing 22% of capric diethylamide, 4.5% of ammonium caproate, 3.5% of lecithin and 70% of white spirit. The composition was diluted in 5 or 6 times its weight of water and neutralised to clean the floor of a factory of the food industry which had been soiled with animal and vegetable fats. The floor was perfectly cleaned and the washed waters were recovered and were found to be non-toxic to flora and fauna, the emulsion being perfectly stable.

EXAMPLE 4

7 parts of isopropylamine and 35 parts of oleic acid were mixed and the whole was neutralised with ammonia to give a mixture of oleic isopropylamide and ammonium oleate which was mixed with lecithin and white spirit to give a composition containing 29% by weight of the amide/ammonium salt mixture, 3.3% by weight of lecithin and 7.7% of white spirit.

The composition was diluted with 6 times its weight of water and then used to clean various vats and cisterns which had contained hydrocarbons, animal fats and vegetable fats. The emulsions formed were non-toxic and biodegradable.

EXAMPLE 5

13 parts of diethanolamine, 18 parts of caprylic acid, and 35 parts of oleic acid were mixed together to give a mixture of the oleate of caprylic diethanolamide and ammonium oleate.

36 parts of this mixture was added to 3.5 parts of lecithin and 60.5 parts of a petroleum solvent to give a composition which was used in the same manner as described for the compositions of Examples 1–4.

EXAMPLE 6

5 parts of lactic acid and 9 parts of 2-ethyl-hexanoic acid were added to 10 parts of dodecylamine and the whole neutralised with ammonia to give a mixture of the 2-ethyl-hexanoate of dodecylamide and ammonium 2-ethyl-hexanoate.

35 parts of this mixture were mixed with 5 parts of lecithin and 60 parts of n-hexane. The composition obtained was used in the same manner as described for the compositions obtained in the above Examples with the same results.

The above examples may be modified in various ways without departing from the scope of the present invention.

What is claimed is:

1. A process for the preparation of a composition for forming hydrocarbons or fats into a biodegradable emulsion comprises admixing more than one mole of a carboxylic acid with a mole of a primary or secondary aliphatic amine or primary or secondary aliphatic amino-alcohol, neutralizing the mixture by the addition of ammonia to bring the pH to about 7, and finally adding to 22.5 to 40 parts by weight of the neutralized mixture 2.5 to 5 parts by weight of a phospho-aminolipid and 55 to 75 parts by weight of a benzenic fraction-free petroleum solvent.

2. A process according to claim 1, in which the amine comprises at least one member selected from the group consisting of monoethylamine, diethylamine, monoethylamine, dimethylamine, dodecylamine, isoproplylamine, n-butylamine, di-n-butylamine, monoamylamine, di-n-amylamine and di-iso-amylamine.

3. A process according to claim 1, in which the amino-alcohol is selected from the group consisting of monoethanolamine, diethanolamine, amino-propanol and amino-butanol.

4. A process according to claim 1, in which the aliphatic carboxylic acid is selected from the group consisting of acetic acid, propionic acid, n-butyric acid, hexanoic acid, caprylic acid, 2-ethyl-hexanoic acid, oleic acid, capric acid, linoleic acid, lactic acid and ricinoleic acid.

5. A process according to claim 1, in which the phospho-aminolipid is lecithin.

6. A process according to claim 1, in which the solvent is selected from the group consisting of white spirit freed from benzenic fractions, n-hexane, n-heptane, n-octane, petroleum ether, a non-benzenic heavy solvent and a mixture thereof.

* * * * *